US010101254B2

(12) United States Patent
Ihara et al.

(10) Patent No.: US 10,101,254 B2
(45) Date of Patent: Oct. 16, 2018

(54) SHELF-PLATE CRACK DETECTING METHOD, HONEYCOMB STRUCTURE DELIVERING METHOD, SHELF-PLATE CRACK DETECTING APPARATUS, AND SHELF PLATE DELIVERING APPARATUS

(71) Applicant: NGK INSULATORS, LTD., Nagoya (JP)

(72) Inventors: Chikashi Ihara, Nagoya (JP); Takeshi Tokunaga, Nagoya (JP); Kazuyuki Yamasawa, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 253 days.

(21) Appl. No.: 15/072,883

(22) Filed: Mar. 17, 2016

(65) Prior Publication Data

US 2016/0282248 A1   Sep. 29, 2016

(30) Foreign Application Priority Data

Mar. 26, 2015  (JP) ................................. 2015-065203

(51) Int. Cl.
*G01N 3/40*  (2006.01)
*G01G 19/52*  (2006.01)

(52) U.S. Cl.
CPC ............... *G01N 3/40* (2013.01); *G01G 19/52* (2013.01)

(58) Field of Classification Search
CPC ...... F27B 1/12; C30B 31/103; F27D 21/0035; G01L 5/007; G01N 3/00; G01G 19/52;
(Continued)

(56) References Cited

U.S. PATENT DOCUMENTS 3,724,575 A * 4/1973 Kutsay ................. G01G 3/1404
                                                              177/211
4,031,366 A * 6/1977 Hartung ................ F01D 21/003
                                                              377/3
(Continued)

FOREIGN PATENT DOCUMENTS

AT           291857 B     8/1971
JP      08-028246 A1     1/1996
(Continued)

OTHER PUBLICATIONS

European Office Action (Application No. 16161659.4) dated Oct. 6, 2017.
(Continued)

*Primary Examiner* — Harshad R Patel
*Assistant Examiner* — Tran M Tran
(74) *Attorney, Agent, or Firm* — Burr & Brown, PLLC

(57) ABSTRACT

A detecting apparatus includes: a lifting mechanism section that is provided with a lifting portion for lifting honeycomb structures and a shelf plate; an actual load value measuring section that measures an actual load value; a total load value calculating section that adds up the plurality of measured actual load value; a total load value determining section that compares a standard total weight value of the honeycomb structures and the shelf plate to the total load value and determines whether to satisfy a total load value determining condition; an actual load value determining section that compares the actual load value to the specified load value and determines whether to satisfy an actual load value determining condition; and a shelf-plate crack determining section that determines that the shelf plate is cracked when the total load value determining condition or the actual load value determining condition is not satisfied.

6 Claims, 5 Drawing Sheets

(58) Field of Classification Search
CPC .... G01G 19/14; G01G 15/00; G01G 2015/00; G01G 13/243; G01M 5/0033; F26B 25/004
See application file for complete search history.

(56) References Cited

U.S. PATENT DOCUMENTS

| | | | | |
|---|---|---|---|---|
| 4,338,056 A * | 7/1982 | Abrahamson | F26B 25/001 | 414/152 |
| 4,875,170 A * | 10/1989 | Sakurai | G01N 21/88 | 340/679 |
| 5,209,313 A * | 5/1993 | Brodrick | G01G 3/1402 | 177/139 |
| 5,224,626 A * | 7/1993 | Hernandez | B28C 7/0436 | 177/251 |
| 5,257,464 A * | 11/1993 | Trevino-Gonzales | F27D 3/0021 | 264/82 |
| 5,321,637 A * | 6/1994 | Anderson | B66C 13/16 | 177/147 |
| 5,359,516 A * | 10/1994 | Anderson | B66C 23/905 | 212/238 |
| 5,557,526 A * | 9/1996 | Anderson | B66C 23/905 | 212/238 |
| 5,644,489 A * | 7/1997 | Hagenbuch | G01G 19/08 | 177/139 |
| 5,837,946 A * | 11/1998 | Johnson | G01G 3/1404 | 177/136 |
| 5,914,187 A | 6/1999 | Naruse et al. | | |
| 6,520,024 B2 * | 2/2003 | Nihei | G01B 5/30 | 73/799 |
| 6,532,421 B2 * | 3/2003 | Miwa | G07C 3/14 | 374/57 |
| 6,715,587 B2 * | 4/2004 | Sittler | B66B 1/3484 | 187/277 |
| 6,777,114 B2 | 8/2004 | Tomita et al. | | |
| 6,993,178 B2 * | 1/2006 | Ozaki | G01N 21/88 | 382/152 |
| 7,171,314 B2 * | 1/2007 | Meyer | G01M 5/0025 | 324/209 |
| 7,505,885 B2 * | 3/2009 | Deobald | G06F 17/5018 | 428/304.4 |
| 8,321,157 B2 * | 11/2012 | Omori | G01R 31/2849 | 324/537 |
| 8,544,338 B2 * | 10/2013 | Pettit | G01N 3/38 | 73/808 |
| 8,707,795 B2 * | 4/2014 | Kittur | G01N 3/32 | 73/774 |
| 8,764,371 B2 * | 7/2014 | Whitfield, Jr. | B65F 3/00 | 414/406 |
| 9,020,786 B2 * | 4/2015 | Rassaian | G01N 3/32 | 702/182 |
| 9,057,658 B2 * | 6/2015 | Norman Rose | G01L 1/146 | |
| 9,091,610 B2 * | 7/2015 | Hisakuni | G01M 7/02 | |
| 9,151,706 B2 * | 10/2015 | Wada | G01N 17/00 | |
| 9,315,970 B2 * | 4/2016 | Chitty | E02F 9/267 | |
| 9,360,383 B2 * | 6/2016 | Coleman | G01L 1/2262 | |
| 9,451,709 B2 * | 9/2016 | Monda | H05K 3/3436 | |
| 9,567,195 B2 * | 2/2017 | Hall | B66C 13/46 | |
| 2003/0021949 A1 | 1/2003 | Tomita et al. | | |
| 2004/0200644 A1 * | 10/2004 | Paine | G01G 19/083 | 177/136 |
| 2006/0009951 A1 * | 1/2006 | Tryon, III | G06F 11/008 | 702/185 |
| 2007/0050271 A1 * | 3/2007 | Ufford | G06Q 10/087 | 705/28 |
| 2010/0131182 A1 * | 5/2010 | Deegan | G01G 19/08 | 701/124 |
| 2015/0226654 A1 * | 8/2015 | de Ketelaere | G01N 33/08 | 702/43 |

FOREIGN PATENT DOCUMENTS

| | | |
|---|---|---|
| JP | 2002-154882 A1 | 5/2002 |
| JP | 2004-051384 A1 | 2/2004 |
| JP | 2007-010208 A1 | 1/2007 |

OTHER PUBLICATIONS

Extended European Search Report (Application No. 16161659.4) dated Jul. 28, 2016.

* cited by examiner

SHELF-PLATE CRACK DETECTING METHOD, HONEYCOMB STRUCTURE DELIVERING METHOD, SHELF-PLATE CRACK DETECTING APPARATUS, AND SHELF PLATE DELIVERING APPARATUS

The present application is an application based on JP 2015-065203 filed on Mar. 26, 2015 with the Japan Patent Office, the entire contents of which are incorporated herein by reference.

BACKGROUND OF THE INVENTION

Field of the Invention

The present invention relates to a shelf-plate crack detecting method, a honeycomb structure delivering method, a shelf-plate crack detecting apparatus, and a shelf plate delivering apparatus. More particularly, the invention relates to a shelf-plate crack detecting method, a honeycomb structure delivering method, a shelf-plate crack detecting apparatus, and a shelf plate delivering apparatus which can detect cracks on a shelf plate used in a firing process for producing honeycomb structures and automate a delivery (remounting) operation of the honeycomb structures.

Description of the Related Art

In the related art, ceramic honeycomb structures are used in a wide range of applications such as a catalyst carrier for purifying exhaust gases of a vehicle, a diesel particulate removing filter, or a heat storage body for a burning apparatus. A forming material (kneaded material) is extruded into a desired honeycomb shape using an extruder and then fired at a high temperature, whereby the ceramic honeycomb structures (hereinafter, simply referred to as "honeycomb structures") are produced.

Various types of the honeycomb structures are produced according to the intended use, and for example, a honeycomb structure having a large honeycomb diameter and a honeycomb structure having thinned partition walls for defining cells is produced.

As a material of the honeycomb structures, ceramics such as cordierite having a very small thermal expansion coefficient or a silicon carbide material having very high thermal resistance is used. Since the diesel particulate removing filter is exposed to a high temperature at the time of incineration and regeneration of trapped diesel particulates, a silicon carbide material is typically used for the diesel particulate removing filter. Since the silicon carbide material has high thermal resistance and large thermal expansion coefficient, it is often fractured at a high temperature by thermal stress during burning and regeneration of the filter. In order to prevent the fracture of the silicon carbide material due to the thermal stress, the filter is divided into small blocks. For example, a honeycomb formed body extruded into a quadrangular shape is fired to prepare honeycomb segments (honeycomb fired bodies), and the plurality of obtained honeycomb segments are combined to each other and bonded to each other using a bonding material, whereby a honeycomb structure (honeycomb block body) having one large block shape is formed (for example, see Patent Documents 1 and 2). Thereafter, a circumferential surface of the honeycomb block body is ground, a circumference coating material is applied to the ground circumferential surface of the honeycomb block body, and a circumferential wall is formed, whereby a honeycomb structure having a large honeycomb diameter is produced (for example, see Patent Document 3).

In a firing process for producing the honeycomb structure, three firing furnaces are used which include: a degreasing furnace for heating and removing organic substances, carbides, or the like contained in the honeycomb structure at a relatively low temperature (for example, about 500° C.) before main firing; a main firing furnace for heating the honeycomb structure, after heating in the degreasing furnace, at a high firing temperature for a long time; and an oxidation furnace for oxidizing a surface of the honeycomb structure, after heating in the main firing furnace, and forming a protective membrane. The firing of the honeycomb structure is completed through the firing process by each of the firing furnaces.

For the purpose of improvement of productivity, a plurality of honeycomb structures is introduced collectively into each of the firing furnaces. Therefore, a stacked body is formed using firing members such as a base plate, a shelf plate, a frame, and a top plate, and the honeycomb structures are accommodated in the stacked body in a state of being stacked in multiple stages, thereby being introduced into the firing furnaces. More specifically, on a bottom base plate having a flat shape, a rectangular shelf plate smaller than the base plate is placed. Then, the plurality of pillar-shaped quadrangular honeycomb structures is mounted on a shelf-plate surface of the shelf plate in a state of being aligned. Thereafter, a cylinder-shaped rectangular frame is installed to surround the mounted honeycomb structures, the frame being constituted by a plate-shaped member having a width larger than a height (corresponding to a width of a side) of the formed body of the honeycomb structure and having a bored inner portion. Then, a new shelf plate is placed on an upper surface of the installed frame.

Thus, the plurality of honeycomb structures are accommodated in a space between the pair of shelf plates spaced apart from each other in a vertical direction by the frame. At this time, since the plate-shaped member constituting the frame is formed to have the width larger than the height of the formed body of the honeycomb structure, the upper surface of the honeycomb structure does not come in contact with a lower surface of the upper shelf plate. As a result, a gap is formed between the upper surface of the honeycomb structure and the lower surface of the shelf plate. Furthermore, a plurality of honeycomb structures is mounted on the surface of the upper shelf plate in a state of being aligned, and a frame is installed at a circumference thereof in the same way. By repetition of the above operation, a stacked body for firing is formed in which the plurality of shelf plates and frames are stacked on the base plate in multiple stages and the plurality of honeycomb structures are accommodated in the space surrounded by the frame and the pair of shelf plates in a state of being aligned. In the top stage of the stacked body, a top plate is placed on the upper surface of the frame instead of the shelf plate. In such a manner, the stacked body is introduced from the inlet of the firing furnace in a state where the plurality of honeycomb structures are accommodated inside thereof.

As described above, each of the degreasing furnace, the main firing furnace, and the oxidation furnace imparts different effects to the honeycomb structures in the firing process. Accordingly, in order that the honeycomb structures obtain a sufficient effect in each of the firing furnaces, the honeycomb structures are introduced into each of the firing furnace in different arrangement manners. That is, the stacked body is introduced each of the firing furnaces with different configurations.

For this reason, between the degreasing furnace and the main firing furnace and between the main firing furnace and the oxidation furnace, it is necessary to perform an operation of delivering (delivery operation) in such a manner that the stacked body led out of an outlet of each firing furnace is once dismantled and then the honeycomb structures mounted on the shelf plate are re-stacked and remounted to conform with a firing furnace to be used in a subsequent process and delivered again to the firing furnace. The delivery operation accompanied by the remounting of the honeycomb structures is mainly performed by hand work of a worker, and is not automatically performed using robots or the like under the present circumstances. At this time, together with the remounting operation, a quality control operation of the shelf plate is performed by visual observation of the worker time determining whether defects such as cracks or chips occur on the shelf plate which is mounted with the honeycomb structures to constitute the stacked body.

[Patent Document 1] JP-A-8-28246
[Patent Document 2] JP-A-2002-154882
[Patent Document 3] JP-A-2004-51384

SUMMARY OF THE INVENTION

A remounting and delivery operation of honeycomb structures have needed to be carefully performed between respective firing furnaces such that defects do not occur in honeycomb structures. In addition, since a shelf plate mounted with the honeycomb structures is heavy, the remounting and delivery operation has also imposed a heavy burden on a worker. Furthermore, since the remounting operation has been performed by hand work, the operation time has become longer, and this has been a factor that a total operation time required for producing the honeycomb structures is prolonged. Therefore, many studies have been attempted to automate the remounting operation of the honeycomb structures to be performed between respective firing furnaces in a firing process for producing the honeycomb structures, for example, using machine equipment such as robots. Thus, it is possible to save labor by reducing the number of workers in the production of the honeycomb structures and form the honeycomb structures effectively and rapidly.

Here, in the case of firing the honeycomb structures by the firing process, particularly, in the case of main firing of performing at a high firing temperature equal to or higher than 1400° C., the shelf plate mounted with the honeycomb structures is cracked when being exposed to the high temperature for a long time and thus a so-called "shelf-plate crack", that means the shelf plate itself is damaged, has routinely occurred. As described above, when the remounting and delivery operation of the honeycomb structures is performed by hand work of the worker himself, it is easy for the worker to remove the cracked shelf plate and remount the honeycomb structures on a newly replaced shelf plate. Therefore, the remounting operation of the shelf plate can be rapidly performed, and this has not become a factor of an operation delay in particular.

However, when the remounting and delivery operation is automated by robots or the like for the purpose of labor-saving and efficiency of the operation, the robots have not had a function of determining whether cracks on the shelf plate mounted with the honeycomb structures occur after the main firing, for example. In addition, specific technique and apparatus for detecting the cracks on the shelf plate have not been clearly defined.

Accordingly, in view of the above circumstances, the invention is to provide a shelf-plate crack detecting method, a honeycomb structure delivering method, a shelf-plate crack detecting apparatus, and a shelf plate delivering apparatus that detects cracks occurring on a shelf plate during a firing process based on predefined determining conditions, can stop an apparatus for delivering the shelf plate if necessary, and can effectively produce the honeycomb structures by increasing a possibility of automating a remounting (delivery) operation of the honeycomb structures.

According to the invention, there are provided the following shelf-plate crack detecting method, honeycomb structure delivering method, shelf-plate crack detecting apparatus, and shelf plate delivering apparatus.

[1] A shelf-plate crack detecting method including: a lifting process of lifting a shelf plate mounted with honeycomb structures using a plurality of lifting portions; an actual load value measuring process of measuring actual load values applied to the lifting portions by which the shelf plate is lifted, for each of the lifting portions; a total load value calculating process of adding up the plurality of measured actual load values and calculating a total load value; a total load value determining process of comparing a prescribed standard total weight value related to a total weight of the honeycomb structures and the shelf plate to the calculated total load value and determining whether the standard total weight value coincides with the total load value; an actual load value determining process of comparing a specified load value to the actual load value and determining whether the actual load value is equal to or larger than the specified load value, the specified load value being obtained by multiplying the standard total weight value by a specified coefficient specified in advance depending on the number of the lifting portions; and a shelf-plate crack determining process of determining that the shelf plate mounted with the honeycomb structures is cracked when at least one condition of the total load value determining process or the actual load value determining process is not satisfied.

[2] The shelf-plate crack detecting method according to [1], wherein the specified coefficient is set by subtracting a measurement error from a standard distribution ratio decided by a prescribed standard mounting position of the honeycomb structure on the shelf plate and a standard lifting position of the lifting portion.

[3] The shelf-plate crack detecting method according to [1] or [2], wherein the lifting portion includes an extension portion extending in proportion to the actual load value.

[4] A honeycomb structure delivering method using the shelf-plate crack detecting method according to any one of [1] to [3], the method including: a stop process of notifying the determination in the shelf-plate crack determining process that the shelf plate is cracked and stopping a delivery of the honeycomb structures due to the shelf plate at the same time; and a shelf plate delivering process of delivering the shelf plate mounted with the honeycomb structures to a predetermined position when it is determined by the shelf-plate crack determining process that the shelf plate is not cracked.

[5] A shelf-plate crack detecting apparatus including: a lifting mechanism section including a plurality of lifting portions that lifts a shelf plate mounted with honeycomb structures; an actual load value measuring section incorporated in the lifting portions to measure actual load values applied to the lifting portions by which the shelf plate is lifted, for each of the lifting portions; a total load value calculating section that adds up the plurality of actual load values measured by the actual load value measuring section and calculates a total load value; a total load value determining section that compares a prescribed standard total weight value related to a total weight of the honeycomb structures and the shelf plate to the calculated total load value and determines whether the standard total weight value coincides with the total load value; a specified load value calculating section that calculates a specified load value obtained by multiplying the standard total weight value by a specified coefficient specified in advance depending on the number of the lifting portions; an actual load value determining section that compares the calculated specified load value to the actual load value and determines whether the actual load value is equal to or larger than the specified load value; and a shelf-plate crack determining section that determines that the shelf plate mounted with the honeycomb structures is cracked when at least one condition of the total load value determining section or the actual load value determining section is not satisfied.

[6] A shelf plate delivering apparatus using the shelf-plate crack detecting apparatus according to [5], including: a delivery stopping section that notifies the determination in the shelf-plate crack determining section that the shelf plate is cracked and stops a delivery of the honeycomb structures by the shelf plate at the same time; and a shelf plate delivering section that delivers the shelf plate mounted with the honeycomb structures to a predetermined position when it is determined by the shelf-plate crack determining section that the shelf plate is not cracked.

According to the shelf-plate crack detecting method of the invention, the honeycomb structures and the shelf plate are lifted to measure the load weight, and the presence or absence of cracks on the shelf plate can be determined according to the predefined determining condition. According to the honeycomb structure delivering method, it is possible to stop the delivery of the honeycomb structures and deliver the shelf plate to the predetermined position, based on the shelf-plate crack detecting method. According to the shelf-plate crack detecting apparatus and the shelf plate delivering apparatus of the invention, it is possible to detect the cracks on the shelf plate according to principles of the shelf-plate crack detecting method and the honeycomb structure delivering method and thus stop the delivery of the honeycomb structures or deliver it to the predetermined position based on the detection result.

DETAILED DESCRIPTION OF THE INVENTION

Figure 1:
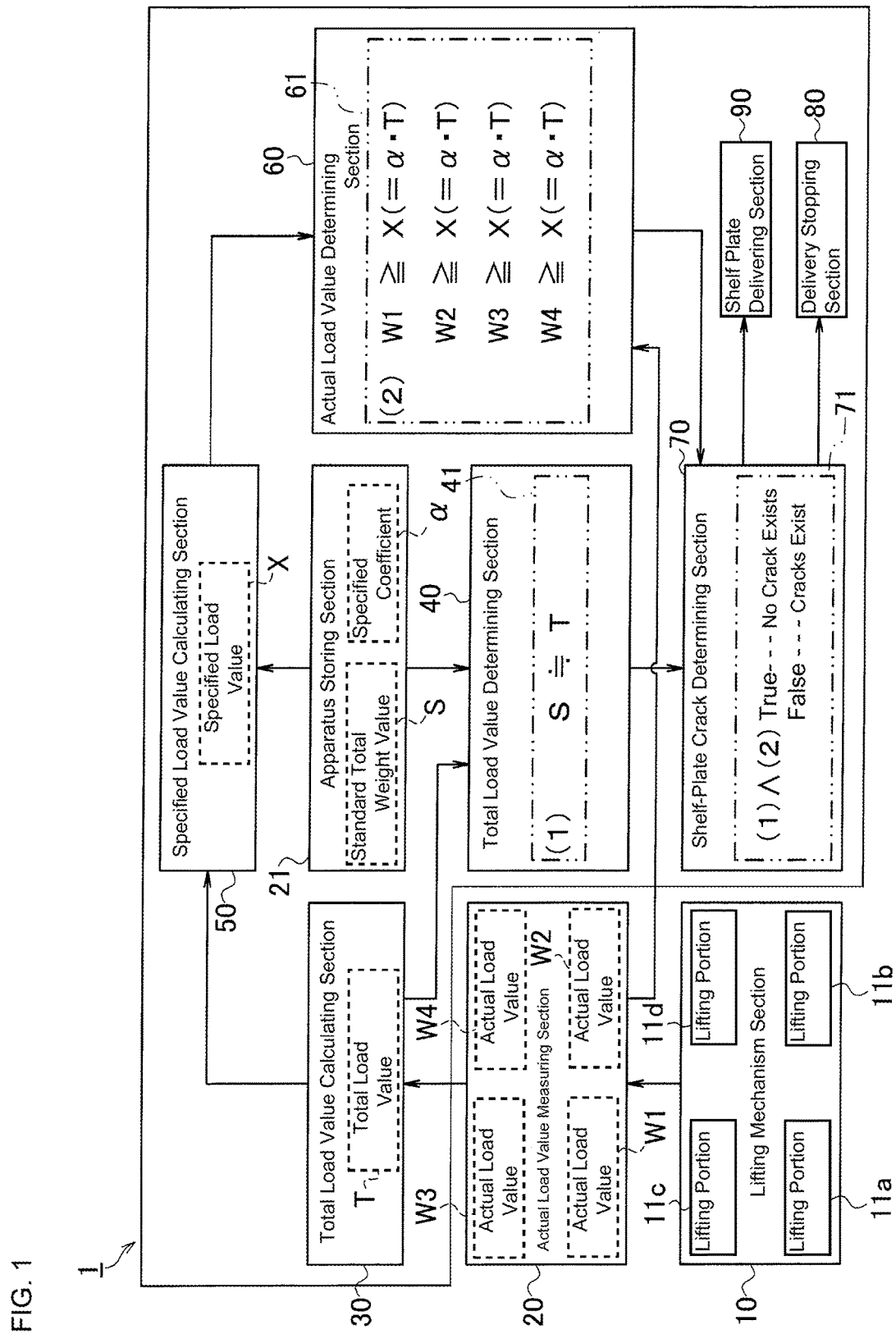
FIG. 1 is an explanatory diagram showing a functional configuration and a determining condition of a shelf-plate crack detecting apparatus and a shelf plate delivering apparatus according to an embodiment of the invention.
Figure 2:
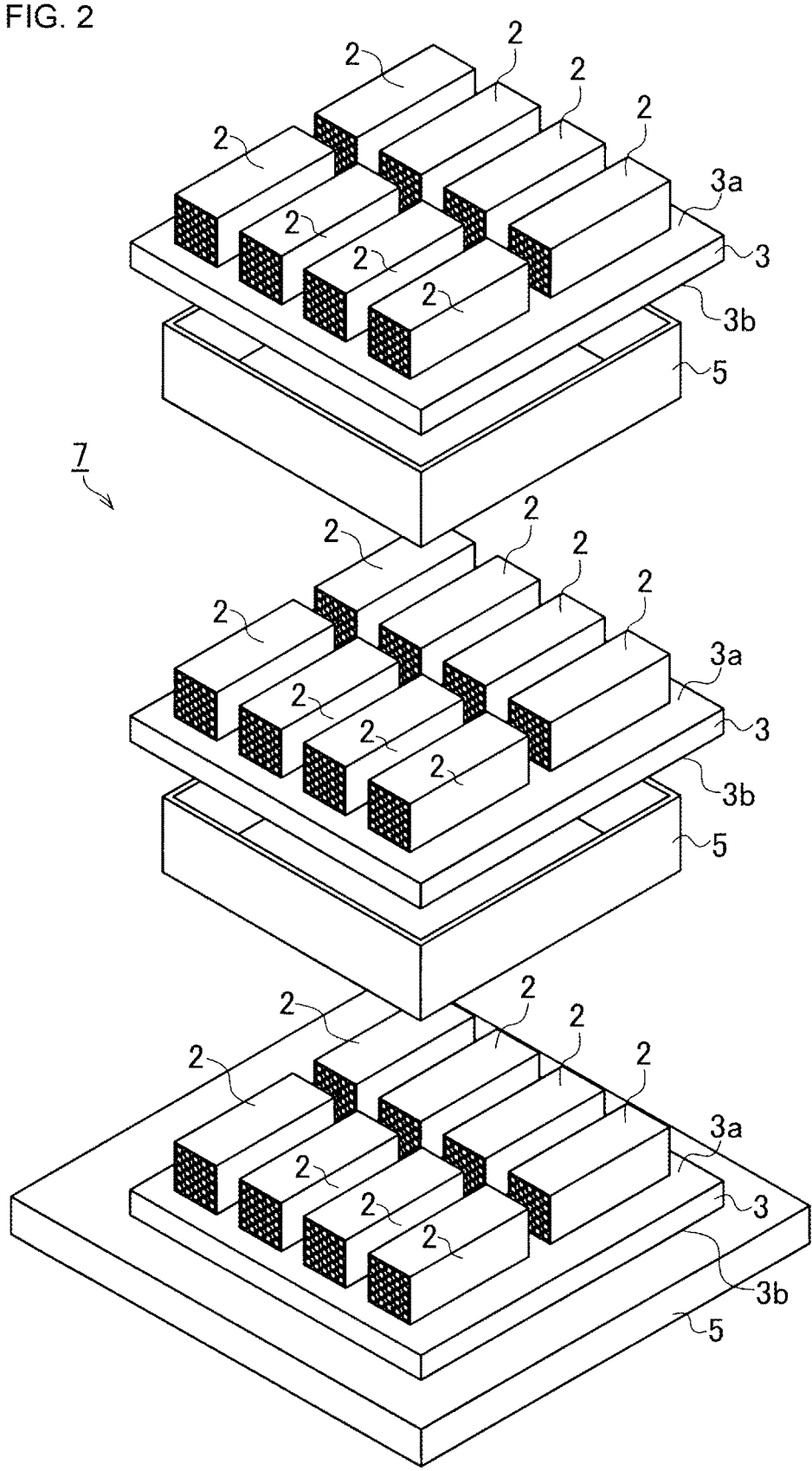
FIG. 2 is an exploded perspective view schematically showing a stacked body and a configuration of honeycomb structures accommodated in the stacked body.

Referring to the accompanying drawings, embodiments of a shelf-plate crack detecting method, a honeycomb structure delivering method, a shelf-plate crack detecting apparatus, and a shelf plate delivering apparatus according to the invention will be described below, respectively. The invention is not limited to the following embodiments, and can be changed, modified, and improved without departing from the scope of the invention.

The shelf-plate crack detecting method according to the embodiment of the invention includes: a lifting process of lifting a shelf plate 3; an actual load value measuring process of measuring an actual load value W1 and the like applied to a lifting portion 11a and the like; a total load value calculating process of adding up the actual load value W1 and the like and calculating a total load value T; a total load value determining process of comparing a standard total weight value S related to a total weight of a honeycomb structure 2 and the shelf plate 3 and a total load value T to each other and determining whether the standard total weight value S and the total load value T coincide with each other; an actual load value determining process of comparing a specified load value X and the actual load values W1, W2, W3, and W4 to each other and determining whether the actual load value W1 and the like are equal to or larger than the specified load value X; and a shelf-plate crack determining process of determining cracks on the shelf plate 3 overall based on the total load value determining process and the actual load value determining process. The honeycomb structure delivering method according to the embodiment of the invention further includes: a stop process of detecting the presence or absence of the cracks on the shelf plate 3 using the shelf-plate crack detecting method and stopping the delivery of the honeycomb structure 2 when the cracks on the shelf plate 3 are detected; and a shelf plate delivering process of delivering the shelf plate 3 mounted with the honeycomb structure 2 to a predetermined position when the cracks on the shelf plate 3 are not detected.

The shelf-plate crack detecting method and the honeycomb structure delivering method according to this embodiment are executed using a shelf-plate crack detecting apparatus 1 (hereinafter, simply referred to as a "detecting apparatus 1") and a shelf plate delivering apparatus to be described below. In this embodiment, for the brevity of the description, the description will be given to a configuration of the detecting apparatus 1 incorporated with the shelf plate delivering apparatus as a part thereof. As shown in FIGS. 1 to 5, the detecting apparatus 1 includes: a lifting mechanism section 10 having four lifting portions 11a, 11b, 11c, and 11d; an actual load value measuring section 20 that measures the actual load values W1, W2, W3, and W4; a total load value calculating section 30 that calculates the total load value T; a total load value determining section 40 that determines based on a total load value determining condition 41; a specified load value calculating section 50 that calculates the specified load value X obtained by multiplying the standard total weight value S by a specified coefficient α; an actual load value determining section 60 that determines based on an actual load value determining condition 61; and a shelf-plate crack determining section 70 that determines cracks on the shelf plate 3 overall. The detecting apparatus 1 further includes: a delivery stopping section 80 that stops the delivery of the honeycomb structure 2 with the shelf plate 3 based on results determined by the shelf-plate crack determining section 70; and a shelf plate delivering section 90 that delivers the shelf plate 3 to a predetermined position. Here, a configuration associated with the delivery stopping section 80 and the shelf plate delivering section 90 corresponds to the shelf plate delivering apparatus of the invention.

The detecting apparatus 1 comprises mainly computing apparatus (a computer) capable of a plurality of arithmetic processing, and the computing apparatus is connected to the lifting mechanism section 10 practically lifting the honeycomb structure 2 and the shelf plate 3 and the actual load value measuring section 20. Furthermore, the detecting apparatus 1 includes an apparatus storing section 21 that stores various types of information or data in advance. Further, various controllers are provided to control a timing and a lifting amount of the shelf plate 3 and the like by the lifting mechanism section 10 or control the measurement of the actual load value W1 and the like.

The detecting apparatus 1 of this embodiment is used at an outlet of a main firing furnace (not shown) in a firing process to detect the presence or absence of cracks on the shelf plate 3 for the purpose of automation of a "remounting operation" to introduce the plurality of honeycomb structures 2 mounted on the shelf plate 3 into an oxidation furnace (not shown) at the subsequent process. In the remounting operation of the honeycomb structures 2 performed between a degreasing furnace and the main firing furnace, the detecting apparatus 1 according to this embodiment may be used. Furthermore, the detecting apparatus 1 can be simply used not for the purpose of introducing the honeycomb structures 2 to the oxidation furnace after the main firing furnace but for the remounting operation of the honeycomb structure 2.

As shown mainly in FIGS. 2 to 5, the honeycomb structures 2 discharged from the outlet of the main firing furnace are accommodated in a stacked body 7 stacked in multiple stages by a plurality of shelf plate 3 and the frame 5. More specifically, on a bottom base plate 4 having a flat shape, the rectangular shelf plate 3 smaller than the base plate 4 is mounted. Then, the plurality of pillar-shaped quadrangular honeycomb structures 2 to be fired are mounted on an upper shelf-plate surface 3a of the shelf plate 3 in a state of being aligned such that one side thereof is brought into contact with the shelf-plate surface 3a.

In this embodiment, a total of eight honeycomb structures 2 (two columns × four rows) are mounted at predefined positions (standard mounting positions) on the shelf-plate surface 3a of one shelf plate 3 at predetermined intervals in such a manner that end faces thereof face each other and longitudinal directions thereof coincide with each other. The number of honeycomb structures 2 to be mounted on the shelf plate 3 is not limited to the above number. Then, the cylinder-shaped rectangular frame 5 is placed on the shelf plate 3 to surround around the mounted honeycomb structures 2, and a new shelf plate 3 is further placed on an upper surface of the frame 5. Thus, the plurality of honeycomb structures 2 are accommodated in a space between shelf-plate surface 3a and a lower surface 3b of the pair of shelf plates 3 spaced apart from each other in a vertical direction by the frame 5. At this time, a gap is formed between the upper surface of the honeycomb structure 2 facing the shelf plate 3 and the lower surface 3b of the shelf plate 3.

Figure 4:
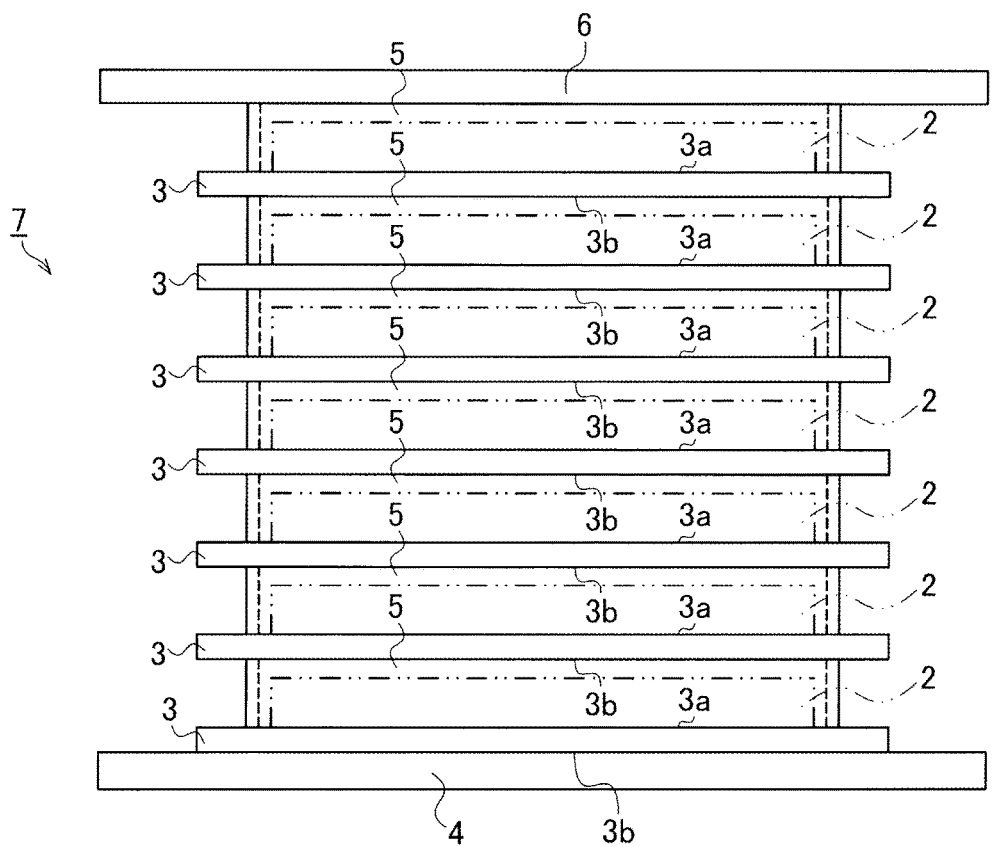
FIG. 4 is a plan view showing a configuration of a stacked body.
Figure 5:
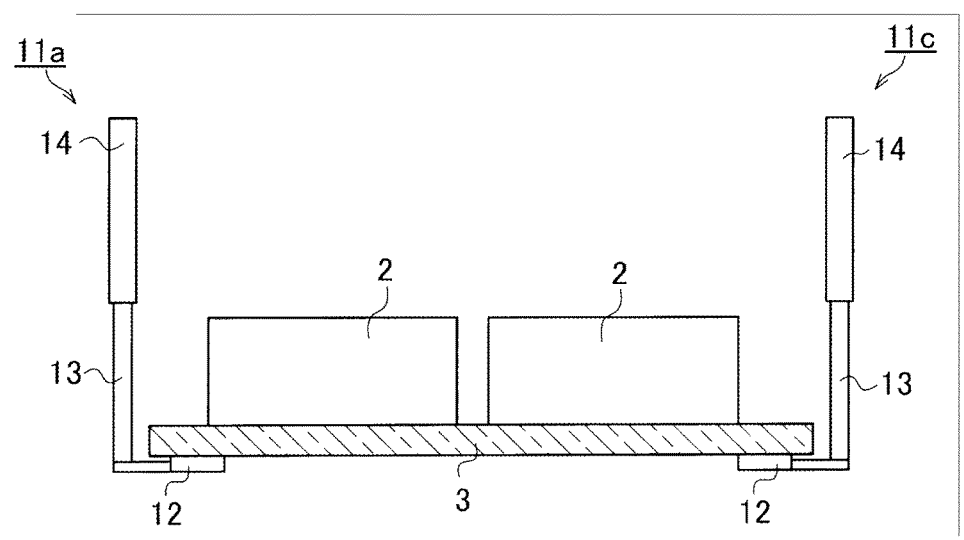
FIG. 5 is a cross-sectional view taken along a line A-A in FIG. 3 showing the state in which the shelf plate and the honeycomb structures are lifted by the lifting mechanism section.

Then, eight honeycomb structures 2 are mounted on the shelf-plate surface 3a of the new shelf plate 3 overlaid on the frame 5 in a state of being aligned as described above, and a new frame 5 is further installed on the shelf-plate surface 3a. Thereafter, a further another shelf plate 3 is mounted on an upper surface of the frame 5. Thus, a combination of the shelf plate 3 and the frame 5 is formed in one stage, and the combination can be stacked in multiple stages. At this time, the plurality of honeycomb structures 2 is accommodated in the each space surrounded by the shelf plate 3 and the frame 5. Thereby, the stacked body 7 having the honeycomb structures 2 to be fired is formed to be introduced into the main firing furnace. As shown in FIG. 4, with respect to the top of the stacked body 7, a top plate 6 is used instead of the shelf plate 3. Here, the shelf plate 3 is mainly made of a silicon carbide material, and each of the base plate 4, the frame 5, and the top plate 6 is made using a refractory material capable of withstanding high-temperature firing by the main firing furnace.

The detecting apparatus 1 of this embodiment detects cracks on the shelf plate 3 by measuring a weight of the honeycomb structures 2 and the shelf plate 3 for one stage in the stacked body 7 according to the above aspect which is introduced the inlet of the main firing furnace and then led out of the outlet thereof after a lapse of a predetermined time. Here, a total weight of the shelf plate 3 corresponding to a portion of one stage and the honeycomb structures 2 mounted on the shelf plate 3 after main firing is calculated in advance, and the total weight thereof is stored in the apparatus storing section 21 of the detecting apparatus 1, as a standard total weight value S. In the stacked body 7 led out of the main firing furnace, the top plate 6 is removed first, and then the frame 5 is also removed. Thus, a lifting operation of the honeycomb structures 2 and the shelf plate 3 located at a top stage can be performed by the lifting mechanism section 10.

Furthermore, in the detecting apparatus 1 of this embodiment, the lifting mechanism section 10 is a mechanism that lifts the shelf plate 3 and the honeycomb structures 2 by a predetermined height (for example, about 5 to 10 mm) from a ground contact surface G (for example, see FIG. 6) to raise them from the mounting surface and comes in contact with the lower surface 3b of the shelf plate 3 at four lifting positions P1, P2, P3, and P4 (corresponding to standard positions) to support the shelf plate 3 and lift (or hoist) it from an under side thereof.

Figure 3:
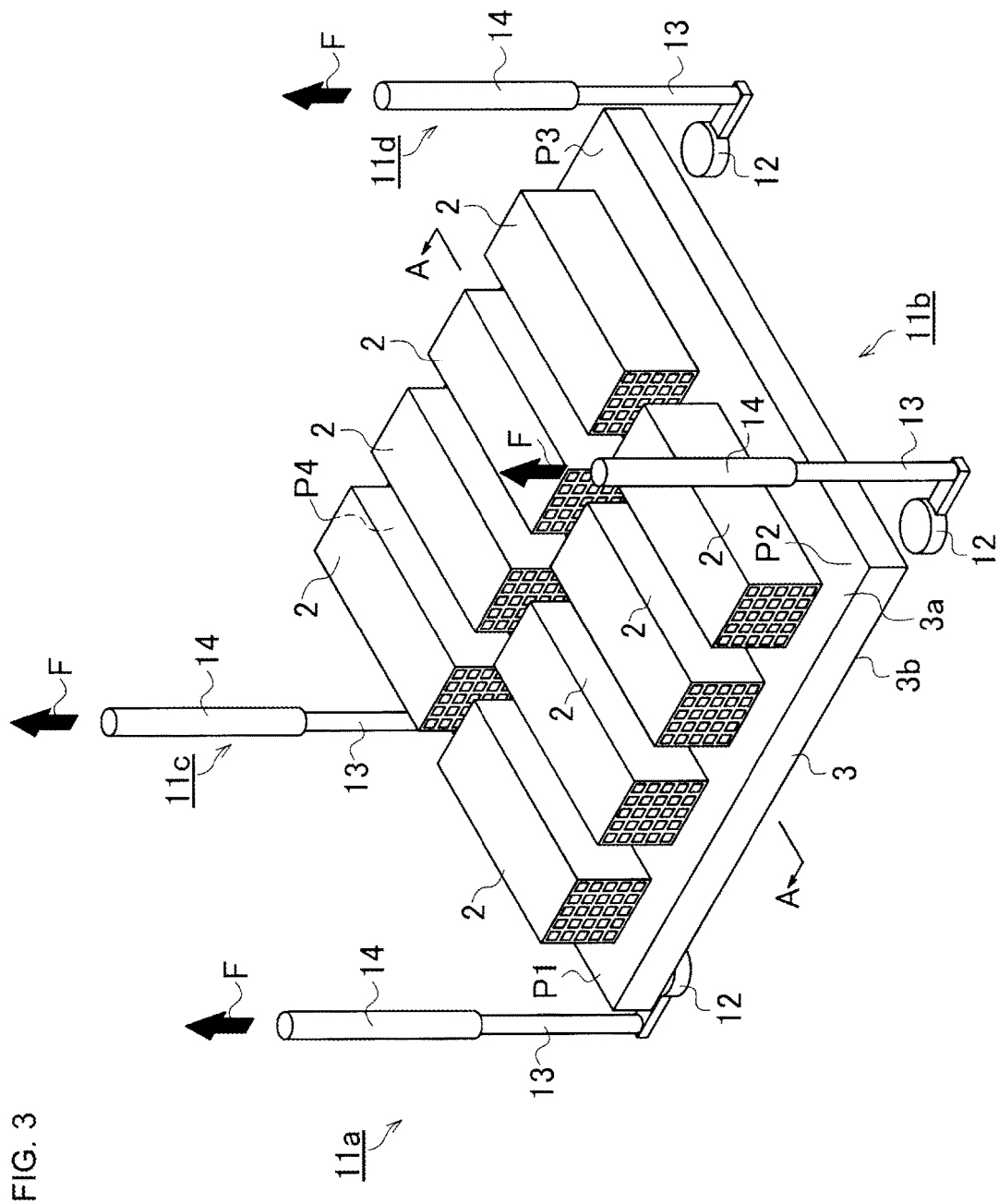
FIG. 3 is a perspective view schematically showing a state in which a shelf plate and honeycomb structures are lifted by a lifting mechanism section.

The lifting mechanism section 10 includes: four lifting portions 11a, 11b, 11c, and 11d that come in contact with the lower surface 3b of the shelf plate 3 at the lifting position P1 and the like and perform the lifting operation; and a lifting driver (not shown) that lifts the lifting portion 11a and the like in an upward lifting direction F (see FIG. 3). The lifting portion 11a and the like are disposed in the vicinity of four corners of the rectangular shelf plate 3 (near angular portions) (see FIGS. 3 and 5). For example, the lifting portion 11a and the like include a disk-shaped contact portion 12 coming in contact with the lower surface 3b of the shelf plate 3 at the lifting position P1, an L-shaped lifting arm 13 extending from the contact portion 12, and a lifting-portion main body 14 extending from one end of the lifting arm 13.

Each of the lifting portion 11a and the like can move upward at a predetermined lifting speed when the lifting driver is activated by transmission of a signal from the controller incorporated in the detecting apparatus 1. At this time, four of the lifting portion 11a and the like of the lifting mechanism section 10 synchronize the lifting speeds with each other and lift the shelf plate 3 such that the shelf-plate surface 3*a* of the shelf plate 3 to be lifted is parallel with a horizontal plane (corresponding to an installation plane of the detecting apparatus 1) (corresponding to the lifting process of the invention). Here, the lifting driver is not particularly limited, and can employ various driving units such as a cylinder mechanism using a pneumatic pressure or a hydraulic pressure or an electric motor mechanism for lifting by driving a motor using an electric power.

In this case, extension portions (not shown) may be provided which respectively extend the length of the lifting portion 11*a* and the like in proportion to the actual load values W1, W2, W3, and W4 such that the shelf-plate surface 3*a* is parallel with the horizontal plane. Thus, it is possible to avoid a state where at least one of the lifting position P1 or the like rises when the shelf plate 3 is warped by weight of the honeycomb structures 2. Thus, the actual load value W1 and the like of the shelf plate 3 and the honeycomb structures 2 can be accurately measured. As a configuration of the extension portion, for example, an expansion mechanism using a spring can be applicable.

In the detecting apparatus 1 of this embodiment, furthermore, the actual load value measuring section 20 is incorporated in the lifting-portion main body 14 to measure the weight of the shelf plate 3 and the honeycomb structures 2 in conjunction with the lifting mechanism section 10. Here, in the detecting apparatus 1 of this embodiment, a "load cell" is used as the related actual load value measuring section 20, the load cell being a kind of sensor for detecting weight or torque. Then, the related load cell measures a load (force) applied to each of the lifting portions during the lifting process, and the measurement result is converted into an electrical signal and read by detecting apparatus 1 (corresponding to the actual load value measuring process).

Specifically, the actual load values W1, W2, W3, and W4 at four lifting positions P1, P2, P3, and P4 (measurement positions) of the shelf plate 3 are acquired by the actual load value measuring section 20 and transmitted to the total load value calculating section 30 and the actual load value determining section 60 of the detecting apparatus 1.

The total load value calculating section 30 adds up the respective actual load values W1, W2, W3, and W4 measured by the actual load value measuring section 20 during the lifting operation of each of the lifting portion 11*a* and the like and performs the arithmetic processing for calculating the total load value T (=W1+W2+W3+W4) (corresponding to the total load value calculating process).

Meanwhile, the total load value determining section 40 compares the standard total weight value S related to the total weight of the shelf plate 3 and the honeycomb structure 2 stored in the apparatus storing section 21 in advance to the total load value T calculated by the total load value calculating section 30 and determines whether to satisfy the total load value determining condition 41 (standard total weight value S≈total load value T) for determining whether the standard total weight value S and the total load value T coincide with each other (corresponding to the total load value determining process).

When cracks or the like do not occur on the shelf plate 3, the standard total weight value S should coincide with the total load value T of the sum of the actual load value W1 and the like obtained by actual measurement. Therefore, it is determined in the total load value determining condition 41 whether the standard total weight value S and the total load value T coincide with each other within a predetermined range. The term of "within the predetermined range" represents a value obtained by adding total weighing accuracy of the actual load value measuring section 20 to variation in individual weight of the honeycomb structures and the shelf plate. Within the above range, the standard total weight value S and the total load value T are determined to be coincide with each other. The predetermined range is set as a range which is ±5% of the standard total weight value S, for example.

Meanwhile, the specified load value calculating section 50 performs the arithmetic processing that calculates the specified load value X obtained by multiplying the standard total weight value S stored in the apparatus storing section 21 by the specified coefficient α set depending on the number of the lifting portion 11*a* and the like. Here, the specified coefficient α is set depending on the number of the lifting portion 11*a* and the like that lift the shelf plate 3 and the honeycomb structures 2. More specifically, the specified coefficient α is set in consideration of an arrangement error and a measurement error from an actual mounting position at which the honeycomb structures 2 are actually mounted on the shelf plate 3, based on a standard mounting position of the honeycomb structures 2 on the shelf plate and a standard distribution ratio determined from the lifting position P1 or the like of the lifting portion 11*a* (corresponding to a standard lifting position in the invention).

The honeycomb structures 2 mounted at the standard mounting position are lifted at the lifting positions P1, P2, P3, and P4 that are four corners of the shelf plate 3, whereby the center of gravity of such a shelf plate 3 exists at the center. Moreover, when it is assumed that there is no arrangement error between the actual mounting position and the standard mounting position of the honeycomb structures 2, the load of the shelf plate 3 and the honeycomb structures 2 is equally applied to each of the lifting portion 11*a* and the like. Therefore, in the case of the detecting apparatus 1 of this embodiment having four of the lifting portion 11*a* and the like, it is assumed that the load of 25% relative to the total load (standard total weight value S) of the shelf plate 3 and the honeycomb structures 2 is ideally applied. On the other hand, the measurement error is assumed during the actual load measurement. The factors of the measurement error include weighing accuracy of the actual load value measuring section 20, a bias of the load between the lifting portions 11*a* to 11*d* caused by the arrangement error of the honeycomb structures 2, and a bias of the load between the lifting portions due to the difference in horizontal level between the lifting portions 11*a* to 11*d*. The specified coefficient α is set to 0.23 in consideration of these factors of the measurement error. In the same conditions, when the number of the lifting portions is two, it is assumed that two loads are ideally applied to each of the lifting portions by 50%, and the specified coefficient α can be set to 0.45 in consideration of the measurement error in a similar way. The specified coefficient α can be appropriately modified depending on the arrangement error of the actual mounting position of the honeycomb structure 2 from the standard mounting position, the standard lifting position, and the number of the lifting portions. When the lifting portions are four points or more, the load distribution is not unambiguously decided. The lifting portions are set such that the load is equally distributed as much as possible. When the number N of the lifting portions is four or more, a distribution load of the remaining three points is determined by assuming equal distribution at N−3 points and the specified coefficient α is set in consideration of measurement error.

The actual load value determining section 60 compares each of the actual load value W1 and the like measured by the actual load value measuring section 20 to the calculated specified load value X (=α×S) to determine whether to satisfy the actual load value determining condition 61 that the actual load value W1 and the like are equal to the specified load value X or are larger than the specified load value X (corresponding to the actual load value determining process). It is assumed that the actually measured actual load value W1 and the like are larger than at least the specified load value X.

Therefore, each of the actual load values W1, W2, W3, and W4 is compared to the calculated specified load value X, and thus it is determined whether the actual load value determining condition 61 is satisfied.

The shelf-plate crack determining section 70 determines overall that the cracks occur on the shelf plate 3 mounted with the honeycomb structures 2, based on an overall determining condition 71, when it is determined that the total load value determining condition 41 or the actual load value determining condition 61 is not satisfied by determination processing in at least one of the total load value determining section 40 or the actual load value determining section 60 (corresponding to the shelf-plate crack determining process).

That is, in the total load value determining condition 41, when the standard total weight value S does not coincide with the total load value T of the actual load value W1 and the like, which are actually measured, the load of the shelf plate 3 and the honeycomb structures 2 is applied to other than the lifting portion 11a and the like. That is, it is considered that the cracks occur on the shelf plate 3 and a part of the lower surface 3b of the shelf plate 3 is grounded to the ground contact surface G. As a result, it is determined that the shelf plate 3 is cracked. Meanwhile, in the actual load value determining condition 61, when the load applied to each of the lifting portion 11a and the like is not equal to or larger than the specified load value X, that is, the load applied to at least any one of the lifting portions (for example, the lifting portion 11a) is extremely small in comparison to others and does not exceed the specified load value X, it is determined that the shelf plate 3 is cracked.

From the determination results based on these two determining conditions 41 and 61, when all conditions are satisfied ("True" in FIG. 1), it is determined that no crack exists on the shelf plate 3. Meanwhile, when any one of the determining conditions 41 and 61 is not satisfied ("False" in FIG. 1), it is determined that cracks exist on the shelf plate 3.

Furthermore, in the detecting apparatus 1 of this embodiment, the delivery stopping section 80 stops the remounting operation (delivery operation) of the honeycomb structures 2 when the shelf-plate crack determining section 70 determines that any one of the determining conditions 41 and 61 is not satisfied (corresponding to the stop process in the honeycomb structure delivering method). That is, when the cracks on the shelf plate 3 are detected, the delivery of the honeycomb structures 2 mounted on the shelf plate 3 to the subsequent process stops. At this time, the stop of delivery is notified to the surrounding workers by a known notification unit such as an alarm sound or lamp at the time of stopping of the delivery. Thus, the workers can know that the cracks on the shelf plate 3 are detected. Then, the workers confirm the fact that the cracks actually occur on the shelf plate 3 and remove the cracked shelf plate 3 by hand work. Thereafter, the detecting apparatus 1 of this embodiment is again activated and performs continuously the process of detecting the cracks on the shelf plate and delivering the honeycomb structures.

Meanwhile, in the detecting apparatus 1, the shelf plate delivering section 90 delivers the shelf plate 3 mounted with the honeycomb structures 2 to a predetermined position when the shelf-plate crack determining section 70 determines that both of the determining condition 41 or 61 is satisfied (corresponding to the shelf plate delivering process in the honeycomb structure delivering method). That is, when it is determined that no crack exists on the shelf plate 3, the honeycomb structures 2 and the shelf plate 3 can be delivered to the subsequent process (for example, oxidation treatment in the oxidation furnace).

As described above, according to the detecting apparatus 1 (including a shelf plate delivering apparatus) of this embodiment and the shelf-plate crack detecting method and the honeycomb structure delivering method using the detecting apparatus 1, it is possible to detect the cracks on the shelf plate 3 with accuracy by measuring the weight of the shelf plate 3 and the honeycomb structures 2, comparing the standard total weight value S to the total load value T calculated from the actually measured actual load value W1 and the like, and further comparing each of the actual load value W1 and the like related to each of the lifting portions to the specified load value X. As a result, it is possible to reduce labor of the remounting (delivery) operation during the firing process of the honeycomb structures 2 mounted on the shelf plate 3 and automate such an operation using robots or the like. Particularly, when abnormality such as cracks occurs on the shelf plate 3, since the abnormality occurrence can be notified to the surrounding workers by, for example, sound or light, a recovery operation can be quickly performed by the workers. Furthermore, since the delivery of the honeycomb structures 2 stops at the time of the abnormality occurrence, the shelf plate 3 causing failures in the next process and the honeycomb structure 2 fired on the shelf plate 3 having a high possibility of any failure can be removed from a production line of the firing process. As a result, it is possible to stably produce and supply the honeycomb structures with high quality.

Examples of the shelf-plate crack detecting method, the honeycomb structure delivering method, the detecting apparatus, and the shelf plate delivering apparatus of the invention will be described below, but the shelf-plate crack detecting method, the honeycomb structure delivering method, the detecting apparatus, and the shelf plate delivering apparatus of the invention is not limited to these embodiments.

EXAMPLES (1) Measurement of Weight of Shelf Plate and Weight of Both Shelf Plate and Honeycomb Structure A weight only of a shelf plate (Examples 1 to 4) and a total weight of a shelf plate and honeycomb structures (Examples 5 to 7) were measured using the lifting mechanism section and the actual load value measuring section of the detecting apparatus, respectively. The total weight of both the shelf plate and the honeycomb structures is measured in an actual firing process. In order to confirm the effect of the invention, however, the weight of only the shelf plate is measured in Examples 1 to 4 to detect cracks on the shelf plate.

In these Examples, the lifting mechanism section of the detecting apparatus provided with four lifting portions as shown in FIG. 3 lifted the shelf plate to a height of about 5 to 10 mm from the ground contact surface in a state where the contact portions of the lifting portions came in contact with four lifting positions P1, P2, P3, and P4 which were set near corners of the shelf plate, respectively. At this time, the shelf plate (or, both of the shelf plate and the honeycomb structures) was slowly lifted so as not to swing in a vertical direction or a horizontal direction. In this lifting state, the loads (actual load values W1, W2, W3, and W4) applied to the respective lifting portions were measured using the actual load value measuring section (load cell). The measured actual load value W1 and the like and the total load value T calculated based on the measured actual load value W1 and the like are summarized in the following Table 1. The standard total weight value S related to the total weight of the shelf plate (or, both of the shelf plate and the honeycomb structures) in Examples 1 to 7 is measured in advance and is stored in the detecting apparatus (see Table 1).

case of Example 2, the specified load value X becomes 629 g. Hereinafter, the specified load value X was calculated in each Example (see Table 1).

(4) Determination Based on Total Value Determining Condition

The total load value T calculated by the above (2) is compared to the standard total weight value S of the shelf plate and the like. For example, in the case of Example 1, the standard total weight value S is 2742 g, whereas the total load value T is 2750 g; both values approximate each other and the total load value T is within ±10% relative to the standard total weight value S. For this reason, it is determined to satisfy the total load value determining condition (=OK). Meanwhile, in the case of Example 2, the standard

TABLE 1

|  |  | Example 1 | Example 2 | Example 3 | Example 4 | Example 5 | Example 6 | Example 7 |
|---|---|---|---|---|---|---|---|---|
| State of shelf plate | | No crack exist | Two-part division | Two-part division (corner) | Three-part division | Two-part division | Two-part division | Three-part division |
| Honeycomb formed body | | Absence | Absence | Absence | Absence | Presence | Presence | Presence |
| Standard weight value (S)/g | | 2742 | 2734 | 2732 | 2643 | 3573 | 3573 | 3482 |
| Actual load value (W1)/g of lifting position (P1) | | 710 | 370 | 0 | 140 | 460 | 520 | 320 |
| Actual load value (W2)/g of lifting position (P2) | | 660 | 320 | 680 | 140 | 440 | 520 | 320 |
| Actual load value (W3)/g of lifting position (P3) | | 700 | 320 | 600 | 140 | 410 | 550 | 300 |
| Actual load value (W4)/g of lifting position (P4) | | 680 | 400 | 680 | 140 | 540 | 620 | 280 |
| Total load value (T)/g | | 2750 | 1410 | 1960 | 560 | 1850 | 2210 | 1220 |
| Specified load value (X)/g | | 631 | 629 | 628 | 608 | 822 | 822 | 801 |
| First determination condition | | 2742 ≈ 2750 (OK) | 2745 ≠ 1410 (NG) | 2732 ≠ 1960 (NG) | 2643 ≠ 560 (NG) | 3543 ≠ 460 (NG) | 3573 ≠ 2210 (NG) | 3482 ≠ 1220 (NG) |
| Second determination condition | W1 | 710 > 631 (OK) | 370 < 629 (NG) | 0 < 628 (NG) | 140 < 608 (NG) | 460 < 822 (NG) | 520 < 822 (NG) | 320 < 801 (NG) |
| | W2 | 660 > 631 (OK) | 320 < 629 (NG) | 680 > 628 (OK) | 140 < 608 (NG) | 440 < 822 (NG) | 520 < 822 (NG) | 320 < 801 (NG) |
| | W3 | 700 > 631 (OK) | 320 < 629 (NG) | 600 < 628 (NG) | 140 < 608 (NG) | 410 < 822 (NG) | 550 < 822 (NG) | 300 < 801 (NG) |
| | W4 | 680 > 631 (OK) | 400 < 629 (NG) | 680 > 628 (OK) | 140 < 608 (NG) | 540 < 822 (NG) | 620 < 822 (NG) | 280 < 801 (NG) |
| Total determination | | No crack exist | Cracks exist | Cracks exist | Cracks exist | Cracks exist | Cracks exist | Cracks exist |

(2) Calculation of Total Load Value T

The total load value T related to the sum of four actual load value W1 and the like, which are measured, is calculated. For example, in the case of Example 1, the actual load value W1 is 710 g, the actual load value W2 is 660 g, the actual load value W3 is 700 g, the actual load value W4 is 680 g, and the total load value T is 2750 g. Similarly, in the case of Example 2, the total load value T is 1410 g. Hereinafter, the total load value T was calculated in each Example (see Table 1).

(3) Calculation of Specified Load Value X

The specified load value X obtained by multiplying the standard total weight value S by a specified coefficient α set according to the number of the lifting portions is calculated in each Example. Here, in these Examples, the shelf plate and the like were lifted using four lifting portions as described above, it was assumed that there is no arrangement error between the actual mounting position and the standard mounting position of the honeycomb structures with respect to the shelf plate, and thus specified load value X was calculated by multiplying the standard total weight value S by the specified coefficient α of 0.23. For example, in the case of Example 1, when the standard total weight value S of 2742 g is multiplied by the specified coefficient of 0.23, the specified load value X becomes 631 g. Similarly, in the total weight value S is 2734 g, whereas the total load value T is 1410 g; both values do not approximate each other and the total load value T is out of ±10% or more relative to the standard total weight value S. For this reason, it is determined not to satisfy the total value determining condition (=NG). Hereinafter, the total value determining condition was calculated in each Example (see Table 1).

(5) Determination Based on Actual Load Value Determining Condition

The specified load value X calculated by the above (3) is compared to the actual load values W1, W2, W3, and W4 measured for each of the lifting portions. For example, in the case of Example 1, the actual load value W1 is 710 g in the lifting position P1, whereas the specified load value X is 631 g; the actual load value W1 becomes larger than the specified load value X. For this reason, it is determined to satisfy the actual load value determining condition (=OK). Similarly, the actual load values W2, W3, and W4 are also compared to the specified load value X, and all of them satisfy the actual load value determining condition in the case of Example 1 (see Table 1).

Figure 6:
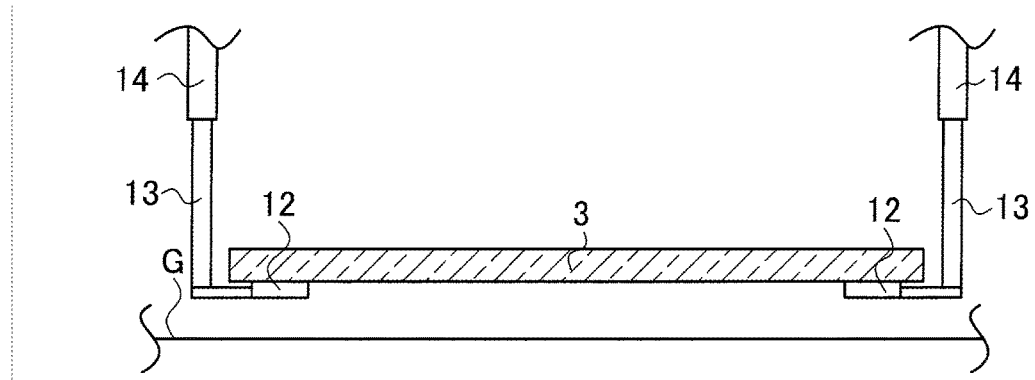
FIG. 6 is a cross-sectional view schematically showing a state in which a shelf plate is lifted in Example 1.

FIG. 6 is a cross-sectional view schematically showing a state in which the shelf plate is lifted in Example 1. In this case, the cracks do not exist on the shelf plate, and all the load of the shelf plate is applied to the lifting portion. For this reason, the total load value T calculated in the above (2) and the standard total weight value S substantially coincide with each other, and the actual load value W1 and the like applied to the respective lifting portions also approximate a value obtained in such a manner the standard total weight value S is equally dispersed and added.

Meanwhile, in the case of Example 2, the actual load value W1 is 370 g, whereas the specified load value X is 629 g in the lifting position P1; the actual load value W1 becomes smaller than the specified load value X and the total load value T is out of −10% or more relative to the standard total weight value S. For this reason, it is determined not to satisfy the actual load value determining condition (=NG). Similarly, the actual load values W2, W3, and W4 are also compared to the specified load value X, and all of them do not satisfy the actual load value determining condition in the case of Example 2 (see Table 1).

Figure 7:
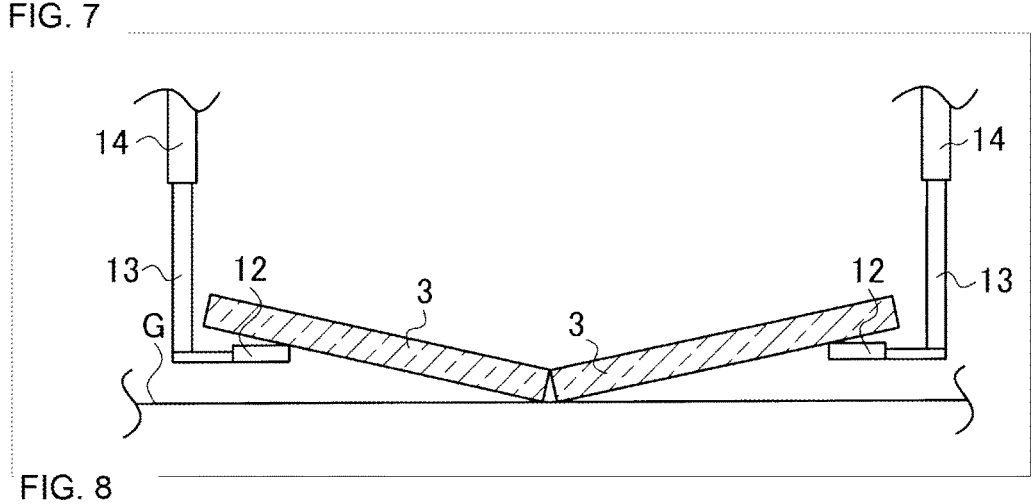
FIG. 7 is a cross-sectional view schematically showing a state in which a shelf plate is lifted in Example 2.

FIG. 7 is a cross-sectional view schematically showing a state in which the shelf plate is lifted in Example 2. In this case, a crack traversely occurs near the center of the shelf plate to divide the shelf plate into two parts. For this reason, a part of the shelf plate comes in contact with the ground contact surface. The contact point with the part of the shelf plate becomes a fulcrum and the shelf plate is lifted by the lifting portion. For this reason, some of the load of the shelf plate is applied to the fulcrum, and thus the actual load value W1 and the like to be measured become smaller. As a result, the total load value T becomes smaller than the standard total weight value S, and each of the actual load value W1 and the like does not approximate the specified load value X.

Further, in the case of Example 3, the actual load value W1 is 0 g, whereas the specified load value X is 628 g in the lifting position P1; the actual load value W1 becomes smaller than the specified load value X. For this reason, it is determined not to satisfy the actual load value determining condition (=NG). In contrast, the actual load value W2 is 680 g, whereas the specified load value X is 628 g in the lifting position P2; the actual load value determining condition is satisfied. The actual load value W3 is 600 g, whereas the specified load value X is 628 g in the lifting position P3; the actual load value W3 becomes smaller than the specified load value X and it is determined not to satisfy the actual load value determining condition (=NG). The actual load value determining condition is satisfied with respect to the W4 (see Table 1).

Figure 8:
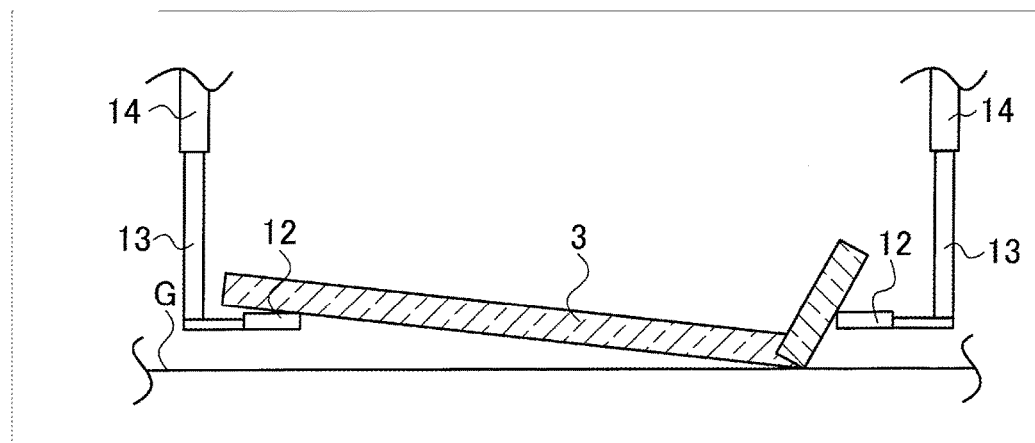
FIG. 8 is a cross-sectional view schematically showing a state in which a shelf plate is lifted in Example 3.

FIG. 8 is a cross-sectional view schematically showing a state in which the shelf plate is lifted in Example 3. In this case, a crack occurs at a part of the corner of the shelf plate to divide the shelf plate into two parts. For this reason, a small piece broken at the corner of the shelf plate drops from the contact portion of the lifting portion, and thus comes in contact with the ground contact surface. Accordingly, the actual load value W1 of the lifting portion from which the small piece drops is not measured, and thus the actual load value W1 becomes 0 g. Meanwhile, a large part of the shelf plate supported by three points of the remaining lifting portions is difficult to lift, and a part of the shelf plate is grounded to the ground contact surface. At this time, the actual load values W2 and W4 measured by the lifting portions of three points satisfy the actual load value determining condition.

(6) Determination of Crack on Shelf Plate

The presence or absence of cracks on the shelf plate is finally determined based on the determination results obtained by each of the determining conditions of the above (4) and (5). That is, when all the determining conditions of the above (4) and (5) are satisfied, it is determined that the cracks do not exist on the shelf plate. Meanwhile, when at least one of the determining conditions of the above (4) and (5) is not satisfied, it is determined that the cracks exist on the shelf plate. That is, in Example 3, the actual load values W2 and W4 satisfy the specified load value X, but the total value determining condition and the actual load value determining condition of the actual load values W1 and W3 are not satisfied. Thus, in this case, it is determined that the cracks exist on the shelf plate.

Example 4 is a case where measurement is performed when cracks occur to divide the shelf plate into three parts, and Examples 5 to 7 is a case where measurement is performed in a state in which the honeycomb structures are mounted on the shelf plate. As indicated in Table 1, in Examples 5 to 7, it is possible to determine the cracks on the shelf plate based on the total load value determining condition and the actual load value determining condition of the invention. Thus, effectiveness is proved by the shelf-plate crack detecting method and the shelf-plate crack detecting apparatus using the method according to the invention that the cracks on the shelf plate could be determined with good accuracy. As a result, the remounting operation of the honeycomb structures can be automated.

The shelf-plate crack detecting method, the honeycomb structure delivering method, the shelf-plate crack detecting apparatus, and the shelf plate delivering apparatus according to the invention can be more advantageously used in the firing process for producing the honeycomb structures capable of being used for a catalyst carrier for purifying exhaust gases of a vehicle, a diesel particulate removing filter, or a heat storage body for a burning apparatus.

DESCRIPTION OF REFERENCE NUMERALS

1: detecting apparatus, 2: honeycomb structure, 3: shelf plate, 3a: shelf-plate surface, 3b: lower surface, 4: base plate, 5: frame, 6: top plate, 7: stacked body, 10: lifting mechanism section, 11a, 11b, 11c, 11d: lifting portion, 12: contact portion, 13: lifting arm, 14: lifting-portion main body, 20: actual load value measuring section, 21: apparatus storing section, 30: total load value calculating section, 40: total load value determining section, 41: total load value determining condition, 50: specified load value calculating section, 60: actual load value determining section, 61: actual load value determining condition, 70: shelf-plate crack determining section, 71: overall determining condition, 80: delivery stopping section, 90: shelf plate delivering section, F: lifting direction, G: ground contact surface, P1, P2, P3, P4: lifting position (standard lifting position), S: standard total weight value, T: total load value, W1, W2, W3, W4: actual load value, X: specified load value, α: specified coefficient.

What is claimed is:

1. A shelf plate crack detecting method using a detecting apparatus comprising: a lifting mechanism section; an actual load value measuring section; and a computing apparatus, which includes a total load value calculating section; a total load value determining section; a specified load value calculating section; an actual load value determining section; and a shelf plate crack determining section;

the method comprising:
a lifting process, in the lifting mechanism section, of lifting a shelf plate mounted with honeycomb structures using a plurality of lifting portions;
an actual load value measuring process, in the actual load value measuring section, of measuring actual load values applied to the lifting portions by which the shelf plate is lifted, for each of the lifting portions, and transmitting each measured actual load value to the total load value calculating section and the actual load value determining section;

a total load value calculating process, in the total load value calculating section, of adding up the plurality of measured actual load values to calculate a total load value;

a total load value determining process, in the total load value determining section, of comparing a predetermined standard total weight value related to a total weight of the honeycomb structures and the shelf plate to the calculated total load value and determining whether the calculated total load value is within a predetermined range of the standard total weight value as a first condition to be satisfied;

an actual load value determining process, in the actual load value determining section, of comparing a specified load value to each measured actual load value and determining whether each measured actual load value is equal to or larger than the specified load value as a second condition to be satisfied, the specified load value being obtained, in the specified load value calculating section, by multiplying the standard total weight value by a specified coefficient specified in advance depending on the number of the lifting portions; and a shelf plate crack determining process, in the shelf plate crack determining section, of determining that the shelf plate mounted with the honeycomb structures is cracked when at least one of the first condition of the total load value determining process and the second condition of the actual load value determining process is not satisfied.

2. The shelf plate crack detecting method according to claim 1, wherein the specified coefficient is set, in the specified load value calculating section by subtracting a measurement error from a standard distribution ratio decided by a prescribed standard mounting position of the honeycomb structure on the shelf plate and a standard lifting position of the lifting portion.

3. The shelf plate crack detecting method according to claim 1, wherein each lifting portion includes an extension portion extending along a length of the lifting portion and in proportion to the actual load value, such that when lifting the shelf plate, the shelf plate is parallel to a horizontal plane.

4. A honeycomb structure delivering method using the shelf plate crack detecting method according to claim 1, the delivering method further comprising: a stop process of notifying the determination in the shelf plate crack determining process that the shelf plate is cracked and stopping a delivery of the honeycomb structures due to the shelf plate at the same time; and a shelf plate delivering process of delivering the shelf plate mounted with the honeycomb structures to a predetermined position when it is determined by the shelf plate crack determining process that the shelf plate is not cracked.

5. A shelf plate crack detecting apparatus comprising:

a lifting mechanism section including a plurality of lifting portions that lifts a shelf plate mounted with honeycomb structures;

an actual load value measuring section incorporated in the lifting portions to measure actual load values applied to the lifting portions by which the shelf plate is lifted, for each of the lifting portions; and a computing apparatus connected to the actual load value measuring section, the computing apparatus including:

a total load value calculating section that adds up the plurality of actual load values measured by the actual load value measuring section to calculate a total load value;

a total load value determining section that compares a predetermined standard total weight value related to a total weight of the honeycomb structures and the shelf plate to the calculated total load value and determines whether the calculated total load value is within a predetermined range of the standard total weight value as a first condition to be satisfied;

a specified load value calculating section that calculates a specified load value obtained by multiplying the standard total weight value by a specified coefficient specified in advance depending on the number of the lifting portions;

an actual load value determining section that compares the calculated specified load value to each measured actual load value from the actual load value measuring section and determines whether each measured actual load value is equal to or larger than the specified load value as a second condition to be satisfied; and a shelf plate crack determining section that determines that the shelf plate mounted with the honeycomb structures is cracked when at least one of the first condition of the total load value determining section and the second condition of the actual load value determining section is not satisfied.

6. A shelf plate delivering apparatus using the shelf plate crack detecting apparatus according to claim 5, the delivering apparatus further comprising: a delivery stopping section that notifies the determination in the shelf plate crack determining section that the shelf plate is cracked and stops a delivery of the honeycomb structures due to the shelf plate at the same time; and a shelf plate delivering section that delivers the shelf plate mounted with the honeycomb structures to a predetermined position when it is determined by the shelf plate crack determining section that the shelf plate is not cracked.

* * * * *